United States Patent
Berg et al.

(10) Patent No.: US 6,610,025 B2
(45) Date of Patent: Aug. 26, 2003

(54) TAMPON APPLICATOR ARRANGEMENT

(75) Inventors: Charles John Berg, Wyoming, OH (US); Jacqueline Ann Daniels, Fairfield, OH (US); Peter Worthington Hamilton, Cincinnati, OH (US); Caroline Stoney Simons, Cincinnati, OH (US); Richard Tweddell, III, Cincinnati, OH (US); Glen Charles Fedyk, Fairfield Twp, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/923,082

(22) Filed: Aug. 6, 2001

(65) Prior Publication Data

US 2003/0028176 A1 Feb. 6, 2003

(51) Int. Cl.⁷ .................................................. A61F 13/20
(52) U.S. Cl. ............................................................ 604/14
(58) Field of Search ........................ 604/11–18, 57–60, 604/311

(56) References Cited

U.S. PATENT DOCUMENTS

| 2,413,480 A | * | 12/1946 | Winter |
| 2,808,832 A | * | 10/1957 | Myers et al. |
| 3,499,447 A | | 3/1970 | Mattes et al. |
| 3,674,025 A | | 7/1972 | Bleuer |
| 3,760,808 A | | 9/1973 | Bleuer |
| 3,791,385 A | | 2/1974 | Davis et al. |
| 4,312,348 A | | 1/1982 | Friese |
| 4,610,659 A | * | 9/1986 | Friese |
| 4,690,671 A | * | 9/1987 | Coleman et al. |
| 4,923,440 A | * | 5/1990 | Genaro |
| 5,569,177 A | | 10/1996 | Fox et al. |
| 5,693,009 A | | 12/1997 | Fox et al. |
| 5,766,145 A | | 6/1998 | Fox et al. |
| 5,769,813 A | * | 6/1998 | Peiler et al. |
| 5,827,214 A | | 10/1998 | Fox et al. |
| 5,928,183 A | | 7/1999 | Fox et al. |
| 5,988,386 A | * | 11/1999 | Morrow |
| 6,036,666 A | * | 3/2000 | Peiler et al. |

* cited by examiner

Primary Examiner—Dennis Ruhl
(74) Attorney, Agent, or Firm—Theodore P. Cummings; Kevin C. Johnson; Bridget D. Ammons

(57) ABSTRACT

The present invention relates to a tampon applicator arrangement, having tampon, applicator unit and a film cap, attached thereto, which is at least partially uniformly shaped, typically being conforming to part or all of the tampon or applicator unit, or such that the film cap has the lowest possible surface area. The film cap is so shaped and/or generally under tension and has no rugosites, folds or even wrinkles, other than optionally tension wrinkles, and preferably also no seams or welds. The invention also relates to specific moulding processes for making the film cap and the arrangement of the invention. The arrangements of the invention provide a smoother, easier and safer insertion of a tampon in the body.

8 Claims, 4 Drawing Sheets

TAMPON APPLICATOR ARRANGEMENT

FIELD OF THE INVENTION

This invention relates to an applicator-tampon arrangement, specifically having a film cap positioned over the tampon or applicator, which has an improved insertion in use. The invention also provides methods for making such applicator-tampon arrangements.

BACKGROUND OF THE INVENTION

A wide variety of absorbent catamenial tampons and applicators have been described. The applicator is typically a device to facilitate the insertion of the tampon into the body. They are typically made from cardboard or plastic. Current commercially available applicators include for example those, which comprise two tubes, telescoped one in another, whereof one tube can move inside the other tube, to push the tampon therein forward and thereby expelling it into the vagina. The applicator is then removed from the vagina, leaving the tampon behind. Another common applicator-tampon arrangement is in the form of a plunger with an inserter tube.

It is of course desirable that the insertion of the applicator is such, that the user does not feel any discomfort while inserting the applicator or while removing the applicator. Many attempts have been made and many solutions have been proposed to provide easier, smoother insertion of tampon-applicators.

In particular, with open-ended applicators, the edge of the inserter tube, which typically enters the vagina first, can be sharp and can scrape and hurt the vagina, or even external body tissue, such as the labia, during insertion. Furthermore, the exposed head of the dry tampon can drag and can make the insertion of the applicator into the vagina uncomfortable. Also, the tube often comprises petals, extending from the top edge of the tube, which are inserted into the vagina and which open when the tampon is pushed out of the tube. The petals are normally sharp and stiff and can hurt the vagina or even external tissue, in particular if a petal is slightly bent out of plane, prior to insertion.

One proposed solution hereto, for example described in U.S. Pat. No. 3,760,808, is to provide the outer tube with a sack of film, which covers this outer tube and thereby makes the outer tube edge less sharp. The tampon can be pushed through said film sack by applying enough pressure on the inner tube. The sack is made by welding films together, and then making lines of weakness, and placing this over the outer applicator, and by inverting the sack onto and down the exterior of the outer tube, to position it between the outer tube and inner tube, as to hold the sack in place.

Whilst such sacks may make the edge of the tube smoother, it does not always result in reduced discomfort for the user. Namely, the sack itself creates other rough edges, rugosites and folds by the way it is applied to the tampon/applicator, thereby leaving spare sack material, which will hinder the insertion of the tampon into the body, hinder the expulsion of the tampon through the film and form potentially sharp folds or wrinkles when introduced in the vagina under pressure. Also, the described sack comprises potentially sharp welds in the sack.

Furthermore, the inventors found that, due to the way the sack-arrangement is formed, e.g. from quite extensible film, the expulsion of the tampon through this type of sack is difficult and it will require the use of a lot of pressure by the user on the applicator, which results in discomfort. The inventors also found that, since this sack is only fixed to the applicator outer tube at the bottom peripheral edge, there is not only a high risk of unintended separation of the sack and the outer tube during insertion, but moreover, there is a problem because this allows the sack film below the tube edge to also extend and thereby increase the extension of the total sack and the work needed to expel the tampon during insertion; both problems occurring in particular since high pressure needs to be used by the user to expel the tampon, due to the construction of the sack-arrangement. Thus, there is a high risk that some or all of the sack comes loose and is left behind in the vagina. Furthermore, the method of making the sack, as described in this document is complex, involving a number of separate steps, including a cumbersome step of inverting the sack when it is applied to the outer tube.

Another method to provide soft insertion of a tampon-applicator arrangement in the vagina is described in U.S. Pat. No. 5,928,183. It is described to provide an applicator which has a specific insertion tip of pleated layers of thin material, folded upon it self, which is said to facilitate expulsion of the tampon. Whilst insertion of a tampon with this applicator may not require large forces, the pleated film can cause discomfort, because the folds can comprise sharp edges, in particular, the topmost portion of the pleat ends are often located at the leading edge of the applicator-tampon arrangement during insertion, and are thus directly in contact with the body, resulting in a high risk of wounding the vagina, labia or other body tissue. Further, during insertion into the body, the pleated film could drag against body tissue; and, inadvertently and pre-maturely fold back or invert away from the tampon head toward the applicator tube thereby causing user discomfort as well as exposing the dry tampon to body tissue during the remainder of the insertion process.

Thus, whilst the provision of such sacks of the prior art can reduce the friction to some extent, providing a smoother insertion, they are not always safe or smooth enough, or raise other problems such as an increase in expulsion force.

The inventors have now found that in order to provide a smooth and safe insertion of the tampon-applicator arrangement, the film cap must be such that it ruptures on a specific moment, when a specific low, maximum force is applied, whilst the cap should still be attached such that it does not leave residues in the body. The improved tampon-applicator arrangement of the inventors has an improved cap construction, which provides an easier, smoother, safer insertion of the tampon-applicator arrangement, and requires a lower force to expel the tampon from the applicator in the vagina.

The inventors have also found an improved process to make applicator-tampon arrangements with a film cap, which is not only a very simple, industrially feasible process, but also results in even smoother, safer and easier to insert tampon-applicator arrangements. The applicator-tampon arrangements obtained by the process have a film cap which conforms to the tampon or applicator with no areas where spare film material can form loose (and often sharp) folds or wrinkles; the arrangements obtained have an improved expulsion profile, reduced risk of leaving film residues (in the body) and reduced risk of harm to the body. Unlike the prior art processes, the process of the invention results (in only one or more separate, industrially feasible, easy process step(s)) in film caps which may even be free of any rugosites or loose folds (e.g. not under tension) or preferably even free of seams and/or welds, and which are thus much smoother.

Thus, film caps can be produced which do not have any uncomfortable and even problematic folds, seams, welds or overlaps, as the sacks of the prior art do. Moreover, by use of the process of the invention, the quality of the film caps formed thereby can be much more controlled, including the provision of the specific expulsion profiles and extension profiles of the film cap and/or arrangement of the invention.

SUMMARY OF THE INVENTION

The present invention relates a tampon and applicator arrangement comprising a tampon and an applicator unit, capable of receiving a tampon, whereby the tampon and applicator unit each have a bottom side and a top portion with a topside, whereby the arrangement has a film cap over or on said tampon or applicator unit, or part thereof, characterised in that the top portion of the film cap, present over or on the top portion of the tampon and/or the top portion of the applicator unit is uniformly shaped, and that said film cap is attached to said applicator.

The invention also relates to a tampon and applicator arrangement comprising a tampon and an applicator unit, capable of receiving a tampon, whereby the tampon and applicator unit each have a bottom side and a top portion with a topside, whereby the arrangement has a film cap over or on said tampon or applicator unit, or part thereof, and whereby said film cap is attached to said applicator, preferably a arrangement as above, being uniformly shaped, characterized in that the arrangement has at least 20% of the tampon exposed at maximum film cap extension (the distance between the topside or point and bottom side or point of the tampon defining the length of the tampon and the distance between the top and bottom side or point of the applicator unit defining the length of the applicator unit).

The invention also relates to a tampon and applicator arrangement comprising a tampon and an applicator unit, capable of receiving a tampon, whereby the tampon and applicator unit each have a bottom side and a top portion with a topside, whereby the arrangement has a film cap over or on said tampon or applicator unit, or part thereof, and whereby said film cap is attached to said applicator, preferably an arrangement as above, characterized in that the film cap is made from a film, typically a formable film, such as a stretchable, plastic yieldable film or even a thermoplastic film. For a film cap made from a stretchable film, i.e. a plastically extensible or plastic yielding film, it is preferred that the film cap is less stretchable (i.e. less plastically extensible or plastic yieldable) than the film, typically having more than 20% or even more than 50% or even more than 60% or even more than 70% or even more than 80% tampon exposed at the maximum film cap extension.

This is beneficial because the film cap formed by stretching a stretchable film can be uniformly shaped and can provide a high percentage of tampon exposed beyond maximum film cap extension during tampon expulsion, which typically requires only a low expulsion force.

The tampon arrangement is typically obtainable by a process comprising the step of first shaping a planar film with a mould of said tampon or applicator, and prior to, simultaneous with or after attaching the thus shaped film cap to said applicator unit, optionally comprising the step of stretching the film cap when shaping the film and/or when attaching the film cap to the applicator unit, thereby creating an area in said film cap which is thinner than said planar film. Hereby, the film cap preferably has a top portion and a collar portion, obtainable by a process as in claim, which comprises the additional step of de-wrinkling the collar portion of the film cap.

The invention also provides such a preferred tampon and applicator arrangement, characterized in that the film cap comprises no folds, welds or seams, but optionally only tension wrinkles.

The arrangement has a very easy and smooth insertion, and a reduced risk of leaving film residues. The arrangement is also such that the film extension does not require too much force, thus reducing discomfort to the user, or leave residues, whilst providing an effective insertion of the tampon.

Preferred is that the cap has a collar portion, which is strain-hardened by a method, described herein. Preferred is that the cap has a collar portion, which is de-wrinkled by a method, described herein. If the skilled person were to try to remove the loose or sharp edges of the sack of U.S. Pat. No. 3,760,808 after application onto the tampon, by use of de-wrinkling, these sacks risk pre-mature rupture; due to the way they are formed.

Preferred is also that the cap has areas of weakness, including thinned areas, to further control the rupture of the film cap and improve the expulsion of the tampon.

The invention also relates to a process for making a tampon and applicator arrangement, as described and claimed herein.

Preferred processes involve the use of a mould, e.g. the tampon or applicator unit itself, or more preferably a male or female mould thereof. Hereby, the male moulding process may be preferred because of the accuracy and ease of processing, whilst the female moulding process may be preferred because the resulting arrangements can yield even lower expulsion forces.

Preferred process steps also involve specific attachment process steps, further film stretching steps, de-wrinkling steps, and strain-hardening steps.

The tampon and applicator arrangement of the invention is preferably present in a protective wrapping, which is removed prior to use of the arrangement.

BRIEF DESCRIPTION OF THE DRAWINGS

FIG. 3b is a cross sectional view of the arrangement of FIG. 3a.

DETAILED DESCRIPTION OF THE INVENTION

Figure 1A:
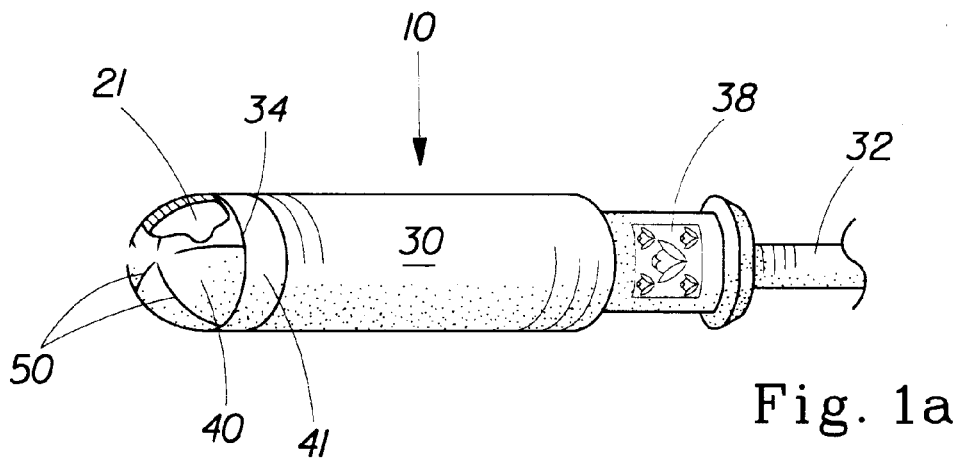
FIG. 1a is a perspective view of a preferred arrangement of the invention.

The tampon and applicator arrangement, hereinafter also referred to as 'arrangement', comprises a tampon, an applicator unit and a film cap. The tampon or at least a part thereof is typically present in said applicator unit, which is typically hollow, to be able to hold a tampon such that a part of the tampon, or the entire tampon, is in the interior (or inside) the applicator unit. Thus, the tampon or a part thereof is covered or enclosed by the unit.

The arrangement of the invention thus comprises at least a film cap, a tampon and an applicator, which comprises an applicator unit. Preferred is that the applicator comprises more than one applicator unit, as described herein after, for example an inserter tube and a push tube.

In one embodiment of the invention, the film cap is at least present over or on the top portion of the tampon, or of the applicator unit; and, the film cap top portion, or even the entire film cap, is uniformly shaped.

This means in one embodiment of the invention, that the film cap conforms to the shape of said tampon top portion or applicator unit top portion, having the smallest possible surface area, e.g. that the film cap is so shaped or under tension, so that it conforms to the smallest possible surface area and that there are no rugosites, such as loose folds or wrinkles, other then optional tension wrinkles, and preferably there are also no seams and/or welds.

In another embodiment of the invention, 'uniformly shaped' means, that at least the portion of the film cap, positioned on the top portion of the tampon or applicator unit, conforms to said portion, and that within this area of close proximity or contact, the surface of the film cap, present on the top portion of the tampon or the top portion of the applicator, is generally parallel to the surface of said top portion and thus, that the distance between the film cap and the tampon or applicator unit is substantially uniform in that area; thus, that there are no areas which extend outwards from the film cap, away from the surface of the said top portion, of the tampon or of the applicator unit, other then optional tension wrinkles, e.g. that there are no rugosites, such as puckers or loose (e.g. not under tension) folds, and preferably that there are also no welds and/or seams.

If the top portion of the applicator unit is positioned substantially completely on the top portion of the tampon, and the film cap is positioned over the top portion of the applicator unit and attached thereto, then typically, the entire film cap is uniformly shaped, and in one embodiment herein, the area of close proximity, or preferably of contact, is typically the complete area where the film cap is present and conforms completely to the applicator unit in this area, and the distance between the entire film cap and the applicator unit is uniform, or preferably zero.

When the tampon or applicator has one or more gaps in the top portion, then it is preferred that either the film cap is not shaped into the gap, in order to remain conforming to the smallest possible surface area, or the film cap may be shaped into the gap in a uniform manner, such that the surface of the cap remains parallel to the surface of the gap, e.g. remains in contact with the tampon or applicator gap. In each embodiment, the film cap remains uniformly shaped, e.g. without rugosites, folds, other then optional tension wrinkles, and preferably even without welds and/or seams.

The uniformly shaped film cap is typically achieved by use of the process described herein and thus typically also applies to the arrangements obtainable by the process described herein.

In one embodiment of the invention, the arrangement of the invention is such that it has at least 20% of the tampon exposed beyond the point of average maximum film cap extension, at the moment the bottom side or bottom point of the tampon is juxtaposed with the top of the applicator unit. Preferably this percentage is at least 30% or even at least 40% or in certain embodiments herein, even at least 50%, or even at least 60%.

This percentage of the tampon exposed, as used herein, is the length of the tampon, relative to the total length of the tampon, which extends beyond the average point/line of the ruptured film cap, which is taken to be herein the average maximum film cap extension (at about the point of rupture), when the tampon bottom side or point is at (juxtaposed to) the edge of the applicator unit.

An arrangement of the invention is obtained and the length of the tampon is determined. The tampon of the arrangement is submitted to a force, namely onto the tampon bottom side or point, to expel the tampon from the applicator unit, through the film cap, thereby rupturing the film cap.

During the experiment, the arrangement is observed, including the moment of the maximum film cap extension, typically about the moment of rupture of the film cap, e.g. by camera and recorded video. It is then determined what the average point (length) of the film cap is at this moment of maximum film cap extension/film cap rupture. Then, the tampon is pushed through the applicator unit up to the moment that the bottom side or point of the tampon is juxtaposed with the highest point of the edge of the applicator unit. Then, it can be determined what the length of the tampon beyond the average point of the film cap is, at the moment of maximum extension, and the percentage this represents of the total tampon length.

If the film ruptures along an uneven line, so that the film cap thus has an non-uniform length at the moment of rupture/maximum film cap extension, then the average length of the film cap at this moment is taken to equal the point, referred to above.

For example, for an arrangement with a tampon which has a total length, from the flat bottom side to the top of the rounded top side or top portion, of 6 cm, and an average maximum film cap extension (average length of rupture line to edge of applicator unit) of 2.0 cm, the percentage tampon exposed as defined herein is (6 cm–2.0 cm)/6 cm×100%= 66.6%.

As an alternative determination, the tampon may be pushed from the applicator unit with a constant speed while recording the time of the start of the pushing of the tampon ($t_0$) and the time of the film cap ruptures, which is observed as above ($t_r$; i.e. the first instance that the film forms a rupture), and then, the average point (length) of maximum film cap extension/rupture can be calculated from the elapsed time $t_r-t_0$ and the known speed, and the percentage tampon exposed can be calculated as above.

Any method to observe or otherwise record the film rupture and travel or exposure of the tampon at that moment may be used, but a preferred method is a maximum expulsion force method, which is also preferably used to determine the maximum expulsion force of the arrangement, as set out below.

This is beneficial because the film cap formed by stretching a stretchable plastic yieldable film can be uniformly shaped and can provide a high percentage of tampon exposed beyond maximum film cap extension during tampon expulsion, which typically requires only a low expulsion force.

Therefore, a preferred embodiment of the invention is a tampon-applicator arrangement, which has a film cap, made from a stretchable plastic yieldable film, which itself is less plastically extensible or stretchable than the film or even non-stretchable, e.g. having more than 50% or even more 60% or even more than 70% or even more than 80% of the tampon exposed at the maximum film cap extension. This may be achieved by forming the cap by stretching the plastic yielding or stretchable film, so that the formed cap itself is less stretchable (or even so that the cap can not be stretched any further), and/or, it may for example be achieved by making a film cap from a stretchable plastic yieldable film and subsequently submitting the formed film cap to a step to reduce the stretchability, for example a strain-hardening step, e.g. to induce plastic yielding. Preferred processes are described herein after.

The maximum expulsion force is the highest force observed during full intended expulsion of the tampon, measured independent of the body (e.g. outside the human body). Therefore, the maximum expulsion force combines all force aspects of the arrangement, including that to rupture and expel the tampon through the film cap/rupture the film. The maximum expulsion force will measure not only the force needed to rupture the cap and expel the tampon through the film cap, but includes other factors such as friction between the tampon and applicator unit. For the arrangements of the invention, the maximum expulsion force is preferably below 2500 grams-force, or even below 2000 grams-force or even below 1500 grams-force or most preferably even below 1000 grams-force or even below 700 grams-force.

In the case when the film cap is strain neutral or strain hardening during extension/tampon travel, the force increases when the film is more extended, reaching the maximum force when the film ruptures. That is, the maximum force occurs at the moment the arrangement also has reached about the (point of) maximum film cap extension. In this case, this can define the point of average maximum film cap extension, as referred to above.

However this maximum force may occur prior to the rupture of the film cap, such as is the case if the film cap is strain softening. Then, the maximum force occurs before the arrangement has reached about the (point of) maximum film cap extension, as referred to above.

As an exemplary measurement method, the maximum expulsion force (and the concurrent observation of the moment of rupture of the film etc, set out above) may be determined as follows.

A tampon-applicator arrangement of the invention is placed in a device, which can measure the peak expulsion force, which is herein held to be the maximum expulsion force, such as (or similar to) a Dillon Force Gauge (Mecmesin AFG50N). The measurement is done by following the operator manual on how to measure the peak force.

The force gauge is oriented such that the load cell 'foot' will travel in the horizontal direction, and it is mounted to a stand and it remains stationary during the test. Also affixed to the stand to one side of the force gauge is a propelled, moveable horizontal slider, controlled by a linear actuator. Attached to the slider is an anchored applicator clamp to hold the inserter unit of the applicator stationary during the test, but without deformation of the applicator. The internal diameter of the clamp is set corresponding the diameter of the inserter unit of the applicator, typically between 12–18 mm.

So when using a telescoping tubes applicator arrangement, when the inserter tube is anchored to the slider by the applicator clamp, the push tube is still free to slide within the inserter tube.

The slider and force gauge are so aligned on the stand that the push tube's longitudinal axis and the force gauge's load cell axis are in-line with each other, in this case a horizontal line. The non-expulsion end of the push tube and the load cell 'foot' are positioned to face each other.

When the slider is actuated, it will move the applicator arrangement towards the load cell foot. The measurement is done at a constant speed setting of the device; a speed of 7.5 cm/sec is an exemplary speed for the test of the arrangements of the invention.

When the slider engages the end of the push tube against the load cell foot, the push tube starts its travel within the inserter tube, first engaging the bottom of the tampon and then expelling the tampon through the film cap. All the while, the force gauge measures the expulsion force, as well as captures the peak expulsion force. The slider stops its movement towards the force gauge after expelling the tampon from the applicator by the operator manually turning off the slider power source (engaging a switch) or using some other form of control, e.g. a travel limit switch, which can cut the power. To one skilled in the art, other fixtures can be constructed using any reliable peak force measurement gauge to measure the expulsion force at a given speed, which is herein referred to as maximum expulsion force.

The device will give a reading for the peak expulsion force, i.e. the maximum expulsion force. By coupling the device to a timer, the time of the start of the experiment defined for calculation purposes as the time the push tube (or other pusher) initially engages the bottom of the tampon, and the time of rupture are monitored, thereby, the extension of the film cap at the moment of rupture can also be calculated.

As a general observation, the maximum expulsion force of the arrangement has been found to be even lower when a female moulding process is used to form the cap, versus a male moulding process, as both described hereinafter.

As used herein the term "tampon" refers to any type of absorbent structure, which is inserted into the vaginal canal or other body cavities for the absorption of fluid there from, or for the delivery of active materials, such as medicaments, or moisture. Preferred herein are catamenial tampons, for insertion in the vagina. As used herein the terms 'vagina' includes the vaginal cavity or vaginal interior and refers to the internal genitalia of the human female in the pudendal region of the body.

Typically, tampons are constructed from an absorbent material, which has been compressed in any or all of the width direction, the radial direction, and the axial direction, in order to provide a tampon, which is of a size and stability to allow insertion within the vagina or other body cavity. The tampon is preferably in a so-called 'self-sustaining' form, e.g. it will tend to retain its general shape and size, before use. This self-sustaining form need not persist during actual use of the tampon. The tampons herein are typically fluid expanding, e.g. the tampon will expand (or un-compress) upon contact with fluid such as bodily fluids.

The tampon has a top portion, having a topside or top (point) and a bottom side or point, both typically positioned, and forming the ends of the longitudinal axis of the tampon. The length is the absolute length from the topside or point to the bottom side or point of the tampon.

The top portion of the tampon is typically the portion, which extends beyond the edge of an open-ended applicator unit, and/or the portion, which extends beyond the (normally substantially transverse) line through the bottom ends of the petals of a petal-containing applicator unit.

The tampon has generally an insertion end and a withdrawal end. The insertion end typically contains or is said topside, whilst the withdrawal end contains said bottom side.

The tampon may be straight or non linear in shape, such as curved along the longitudinal axis. If the tampon is straight, the length of the tampon is between the top portion and bottom side and is generally parallel to the longitudinal axis of the tampon.

If the tampon is curved, the length is the absolute length between the topside and bottom side, thus measured along the curved line (longitudinal axis), which typically curves in an equal manner as the tampon.

The tampon has a width, which may vary in different portions of the tampon. If the tampon is straight, the transverse axis of the tampon is preferably perpendicular to the longitudinal axis and then the tampon width is typically perpendicular to the length.

Often, the tampon is typically cylindrical, having preferably an endless sidewall or endless longitudinal side, preferably with a flat bottom side and a rounded or dome-shaped top portion; then, the width of the tampon corresponds to the largest cylindrical cross-section diameter, and the length corresponds to the distance between the bottom side and the top of the rounded portion.

The tampon may be a non-layered, uniform structure, or it may be a laminar structure comprised of integral or discrete layers, or the tampon may have a folded structure, or it may be rolled, or any other of the structures which are known in the art. Generally, the tampon herein has to have a certain minimal rigidity, to facilitate the expulsion through the film cap.

The tampon may be constructed from a wide variety of liquid-absorbing materials commonly used in absorbent articles such as rayon, cotton, or comminuted wood pulp which is generally referred to as airfelt. Examples of other suitable absorbent materials include creped cellulose wadding; meltblown polymers including co-form; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these. Preferred absorbent materials comprise cotton, rayon (including tri-lobal and conventional rayon fibers, and needle punched rayon), folded tissues, woven materials, nonwoven webs, synthetic and/or natural fibers. The tampon and any component thereof may comprise a single material or a combination of materials. Acceptable types of rayon include GALAXY Rayon (a tri-lobed rayon structure) available as 6140 Rayon from Acordis Fibers Ltd., of Hollywall, England and SARILLE L rayon (a round fiber rayon), also available from Acordis Fibers Ltd. Suitable cotton material includes, long fiber cotton, short fiber cotton, cotton linters, T-fiber cotton, card strips, and comber cotton.

Additionally, superabsorbent materials, such as superabsorbent polymers or absorbent gelling materials may be incorporated into the tampon.

The absorbent material may be surrounded with a liquid permeable material, if desired. Such materials may comprise rayon, cotton, bi-component fibers, or other suitable natural or synthetic fibers known in the art. Rayon, polyethylene, polypropylene and blends of these are particularly suited for use as cover material.

It is desirable that the tampons of the present invention are made in the absorbency ranges, which are currently required, by the United States Food and Drug Administration and corresponding agencies of many other governments, which regulate tampon absorbency.

The tampon typically contains a withdrawal cord or string, which is generally attached to at least the withdrawal bottom portion of the tampon. This may be any type of withdrawal cord known in the art, for example a generally braided (or twisted) withdrawal cord. A conventional type of withdrawal cord (in terms of thickness, material composition, etc.) may be periodically braided with a thicker slub of absorbent fibrous material, which acts as an absorbing member, to form a structure to be connected to the remaining of the tampon. In such an embodiment, the portion of the cord, which will act as the withdrawal cord, may be treated to make it non-absorbent or even hydrophobic. It may also be a withdrawal cord as described in commonly assigned and co-pending U.S. Application Ser. No. 09/309,467, filed on May 10, 1999 in the name of Taylor et al.

The tampon may contain any additional functional ingredients, such as antimicrobial agents, lubricants, antioxidants etc, as known in the art.

The tampon is inserted through the use of an applicator comprising an applicator unit. Any known applicator may be used for insertion of the tampon of the present invention, including commonly known tampon applicators. However, of course for insertion of the tampon in body parts such as the vagina, the applicator should be hygienically designed.

The applicator may be made of plastic, paper, cardboard or other suitable material. Preferred other materials include degradable or compostable thermoplastic materials, preferably water dispersible or water-soluble materials, preferably biodegradable materials, as known in the art.

The applicator may be a combination of a so-called plunger and an applicator unit, whereby the applicator unit is typically a cylindrical tube, capable of holding the pledget or the tampon, or part thereof. Such an applicator unit also typically has gripping means at the trailing bottom end (versus insertion top end).

Then, in a common design, the insertion of the tampon is accomplished by grasping and holding a gripping means, then pushing the rear end of the plunger towards the gripping means. The force used during the pushing forces the plunger or applicator unit to contact the tampon and then forces the tampon to travel through the film cap. That is, during insertion of the tampon into the vagina, the plunger is depressed into the first applicator unit, against the tampon therein, and the traveling expelling tampon may initially extend the film cap, but then ruptures the film cap, so that the tampon itself is introduced into the user's vagina.

One preferred applicator type is a so-called telescoping arrangement, whereby two units or more can move in or around one another, like a telescope, one of which may have gripping means. The units are preferably semi rigid, like cardboard or rigid like plastic. They are typically cylindrical shaped, typically like (at least partially) hollow tubes. A first applicator unit (tube) may then contain or hold part of or the entire tampon, and a second applicator unit (tube) can move inside the first applicator unit, and engage the tampon, thereby pushing the tampon out of the first applicator unit.

Highly preferred is an open-end (flushable) applicator, such as a two-piece telescoping, cardboard assembly with the first applicator unit (or inserter tube) holding the tampon or part thereof, having an open end, where out the tampon can be expelled, and an opposite end, where the second applicator unit is located. The second applicator unit (or pusher tube) has a smaller diameter than the (first unit or) inserter tube, so that it fits inside said opposite end of the inserter tube. This pusher tube is used to push on the back end of the tampon to expel the tampon through the open end of the inserter tube.

Preferred may be that the applicator is flushable through the toilet. Preferred are applicators with tube-shaped applicator units. Preferred may be that the applicator comprises one or more applicator units, which are produced from a spiral-wound paperboard construction, and which are preferably coated on the exterior with a coating material, such as wax. Preferred applicators are also exemplified herein with reference to the figures.

The applicator may have inwardly tapering flexible segments at its top portion to form a normally closed, smooth, openable top. Such segments may be positioned over the film cap (the film cap being between the segments and the tampon top portion) or under the film cap, i.e. between the film cap and the tampon top portion, the latter being preferred. Typically, the segments of the top portion of the applicator are in the form of petals, which form a substantially closed top prior to use, but which can open in the form of individual petals, when a force is applied to them. The film cap attachment to the applicator may be to the segments, or main body of the applicator, or both.

Alternatively, the segments of the top portion of the applicator may not fully extend to the top of the tampon top portion thereby only covering a portion of the tampon top portion, such as in a form of shortened petals. In this case, the film cap may be located above or below the segments. The film cap may cover just the area of the segments, or the area of the applicator top, where the segments do not cover the tampon at the gap, or both.

However, it may be preferred that the applicator has no such segments and that the top portion of the applicator is open ended or at least partially open ended, the open end being covered by (part of) the film cap.

The film cap may be made of any type of (planar) film, which is a flexible and/or deformable substrate, the film typically being a sheet-shaped substrate.

Preferred film materials include paper, woven and non-woven substrates, cloths, metal foils, cellulose fibre sheets, and more preferably organic polymeric materials.

The film materials may be homogeneous in nature or comprise layered structures of two or more film materials joined to each other in a horizontal side-by side arrangement, via for example lap or edge-to-edge butt joints, to form the film used herein. Such joined materials may leave a weld or seam, though care should be taken to minimise the length, width and height of such welds. Preferred may even be that the welds are flattened out, or covered by a coating, prior to use of the joined film to make the film caps herein.

Preferred films are made of one or more of the following substrates and resins: polyolefins, cellulose materials and derivatives, including cellulose ethers, ethyl and/or methyl celluloses, cellulose esters, including cellulose acetates, and/or formates, vinyl polymer derivatives, or more preferably cellophane and/or polyethylenes, polypropylenes, PET, PVC, latex, nylon, polyesters, polystyrenes. Preferred resins and films include polylactides, polyesteramides, aliphatic esters, aliphatic-aromatic copolyesters, polyhydroxyalkonoates, polyalkulene succinate, polyvinylalcohols, cellulosic polymers, starch-based materials and/or polycaprolactone.

Polyolefin, such as polyethylenes and polypropylenes and/or biodegradable films are highly preferred. Preferred polyolefins are also described and defined in "Plastics and Films", chapter 2, by J. H. Briston, $3^e$ edition, published in 1988, Langman Scientific & Technical.

Preferred film and resin examples are: BAK 1095 (available from Bayer), Eastar Bio (available from Eastman Chemicals) for example a blown 37 micron Eastar Bio film, Mater-Bi (available from Novamont), Biomax (available from DuPont), Bionelle (available from Showa High Polymer), Lunare SE (available from Nippon Shokubai), EcoPLA (available from Dow Cargill), Exoflex (available from BASF), Biotec (available from Kashoggi), Vinex (available from Air Products), cellophane, (available from UCB films including the low stretchable or low yieldable uncoated cellophane of about 24.3 microns thick), LACEA (available from Mitsui), and HDPE film available from Tredegar.

Highly preferred olefin films include in particular linear low density polyethylenes (LLDPE) and low density polyethylenes (LDPE) as available from Clopay and high density polyethylenes (HDPE) as available from Tredegar, including for example LDPE film of 25 microns nominal thickness, called DH215 available from Clopay.

The film and the film cap may be porous, non-porous, or micro-porous; the film and film cap may be gas and/or water permeable; the film and film cap may have a low or high critical surface tension; the film and film cap may be hydrophobic or hydrophilic, thermoplastic, and/or thermosetting. Preferred may be that the film is hydrophilic or even water-soluble, water-disintegratable, or water-dispersible and/or preferably thermoplastic or thermosetting. Thermoplastic films are preferred herein, in particular for the female process described herein after.

However, depending on the process used, the film and film cap may be such that it shrinks upon exposure to heat or application of pressure or vacuum. Preferred may be single or biaxially-oriented films, such as polypropylenes.

The film may be made by any process, including casting, extrusion or blow extrusion processes. The film and film cap may comprise, on one or each surface, a functional coating, for example a coating to change the hydrophilicity, hydrophobicity, coefficient of friction, heat sealing properties, gas and/or water permeability, colour, tactile feel and/or odour.

The film may be a highly extensible film. Preferably the highly extensible film has an elongation at break in the machine direction of at least 150%, preferably from 200% to 1000%, or even from 350% to 850%. Typically, the elongation at break in the cross-machine direction is in the same range as mentioned above. Depending on the process and desired film cap rupture profile, it may be preferred that the machine direction and cross machine direction elongation at break be within a similar range. An example of a preferred material is polyethylene DH215, available from Clopay, which has an elongation at break in machine direction of about 630% and in cross machine direction of about 765%. The percentages are average percentages, taken as an average of at least 5 samples. The elongation at break can easily be determined by the skilled person using ASTM D882.

Example of low extensible or non-extensible films include certain types of metallic foils, fibrous paper, cellophanes, woven and non-woven substrates. The film may be made of a strain softening film, as described above, which is such that the arrangement of the invention reaches the maximum expulsion force before rupture of the film. However, more preferred are film caps, which are made of strain hardening films.

In one embodiment of the invention, the film used to make the film cap, and thus the resulting film cap, has no welds or seams. For the purpose of the invention, this definition applies typically to the film prior to shaping it in a film cap with a mould, and to the resulting cap, prior to attachment, and this does not include any means used to attach the film cap to the applicator, which may include for example a welding step, although it is highly preferred that even when the film cap is attached to the applicator, there are no welds present as attachment means, for example in the collar area. Of course, preferred is that the attachment does also not result in any seams in the cap.

The film cap herein has typically a collar portion and a top portion. The top portion is the portion positioned over or on the top portion of the tampon, and/or the corresponding part of the applicator unit, such as when the applicator unit partially or completely covers or surrounds the tampon. In a preferred embodiment the top portion of the film cap is the portion which extends from the top or leading end of the open-ended applicator unit, and/or the top portion is typically the part of the film cap, which is not attached to the applicator, while the collar portion is the portion of the film cap which is attached to the applicator.

The top portion may have a top or topside which is, when the film cap is rounded or dome shaped, typically the area around the highest point of the cap, or when the film cap is not rounded, the top is the area comprising the highest point of the film cap.

The film preferably has an initial thickness, e.g. prior to formation of the film cap, between 1 and 200 microns, preferably from 5 to 100 microns or even from 10 to 75 microns, or even from 15 to 50 microns or most preferably from 20 to 40 microns. This film thickness is the calliper, measured as set out herein.

The film typically has an about homogeneous thickness prior to shaping it into the film cap. However, variations in the thickness of the film can be created by a multitude of techniques including by use of embossing the film during manufacturing; applying a coat extrusion of varying thickness to a base film; creating a film from two or more substrates of different thickness, joined together as described above. The thickness of the film may vary from one area to the next. Such areas may be very small, for example less than 5% or even less than 3% or even less than 1% or even less than 0.5% of the total surface of the film cap, or they may be larger areas.

The thickness variation may be at least 10% or even at least 20%, preferably at least 40% or even at least 60% or even at least 80%, i.e. one area may be a thin area and 10% thinner than another, thicker area, so that the thickness variation between these to areas is 10%. The film can even contain a single or multiple breaches (i.e. no thickness at those points) including holes, perforations, slits, gaps, voids, openings, punctures, cracks, apertures, pores, etc. As is described herein, thinner or weakened areas are often preferred to provide for a controlled and lower expulsion force. However, preferred in many situations is, to utilise the process to make the film cap to induce thinner or weakened areas, whilst a film with uniform thickness is shaped/stretched, as described herein.

Comparing the thickness of part of the film cap to the original thickness of the film, there is preferably at least an area of the film cap, which has a thickness which is at least 10% less than the original thickness of the corresponding area of the original film.

The film cap preferably has areas of weakness, which facilitate the rupture of the film cap. Preferred may also be that the film cap has areas of weakness which are positioned such that the film cap opens in two segments, or for example in the form of petals.

Preferably, the areas of weakness are located in at least a part of the top portion, or only in the top portion of the film cap. Preferred is that the areas of weakness are located such that the top portion of the film cap is opened at more than one place or along more than one rupture line. However, the film cap top portion may open along one line, but then it is preferred that this single line is not an arc over the geometrical top of the film cap, dividing the film cap in two symmetrical halves.

But, more preferred for a cap with a single rupture line is that the cap is such that the rupture is caused in or nearer the area of the film cap which is attached to the applicator, e.g. nearer the bottom periphery of the top portion of the film cap near the collar, leaving a part of this periphery area attached to the applicator, and avoiding that a part is severed from the rest of the film cap. This type of rupture pattern can result in the appearance of a top portion 'lid' where the partial peripheral area of the attachment acts like a 'hinge'. This can for example be achieved by having lines of weakness run in perpendicular direction thereto, e.g. orthogonal to the longitudinal axis of the tampon and typically parallel to the top edge of the collar portion.

Preferred may also be that part of the film cap is cylindrical having a rounded top portion and that it has areas of weakness in the form of one or more continuous or discontinuous lines, which are positioned substantially radially in at least the top portion.

The areas of weakness may be perforations, as known in the art. More preferred may be slits or pinholes, or combinations thereof. The slits and/or perforations are preferably such that the top of the top of the top portion does not comprise any slits or perforation, being blank or optionally comprising one or more pinholes.

More preferably, the areas of weakness are due to variations of thickness in the film cap, e.g. weakness areas where the film cap is thinner than in surrounding areas. This type of cap can provide full hygienic coverage of the tampon top, whilst providing easy rupture of the film cap. The variations in thickness can comprise lines of weakness, but typically comprise larger areas of the film cap, such as those achieved by the processes described herein.

Thickness variations can be determined by comparing the thickness or gauge of one area to an adjacent area. At least 10%, or even at least 20% variation is desirable, preferably at least 40% or even at least 60%. The variation in the thickness of the cap can be measured by any suitable common technique. For large areas, a calliper gauge may be suitable. A suitable method for larger areas is as described in U.S. Pat. No. 6,231,556. For smaller areas, a more microscopic technique is required, for example embedding the film cap in a setting resin, making thin cross section slices of this embedded film cap and measuring the thickness or gauge of the film cap in this cross section by use of for example a scanning electron microscope (SEM).

Variations in thickness may be obtained by using an embossed film, having embossed areas, which are thicker or thinner than surrounding areas. More preferred may be that that the variation in the thickness is achieved by stretching a plastic yieldable film. The area or areas of weakness may thus be achieved during the shaping process of the film cap, typically by shaping the planar film into or over a mould and thereby stretching the film, so that thinning of the film occurs in certain areas, which then subsequently form thinned areas of weakness. Preferred weakness areas in the top portion of the film cap may thus be obtained when a female molding process is used, whereby a film is pulled into a female mould by application of heat, vacuum, solvent or combination thereof, preferably at least by use of vacuum.

Preferred may be that at least the top portion of the film cap is thinner. This can in particular be achieved by using the female moulding process as described herein. It may also be preferred that the film cap has areas of weakness, just above the collar portion, but not on the top of the film cap. This can for example be achieved by using a male moulding process and/or by using a stretching step when attaching the formed film cap to the applicator.

For film caps which are cylindrical and typically round or dome-shaped at the top, preferred shapes of weakness areas lines or interrupted lines lead from the top of the film cap toward the portion of the film cap, which is attached to the applicator, e.g. the collar portion, and divide the film cap in petals of the same or different shapes and/or dimensions. For example, 3, 4, 5, 6 or 7 petals may be formed, most preferably 3, 4 or 5. For example, a film cap with 3, 4, or 5 identical petals of about triangular shape transposed onto a partially spherical surface may be formed, with 3, 4, or 5 (interrupted) lines of weakness, whereby the lines of weakness may converge at the top of the film cap.

Preferred may also be spiralling (interrupted) lines of weakness, dividing the film cap in paisley-shaped petals or wave-shaped petals. Preferred areas of weakness and patterns thereof are also shown in the figures herein.

The film cap preferably has a collar portion, which is substantially free of rugosites, loose folds or even without wrinkles, and thus is substantially smooth, which is obtainable by an additional process step of de-wrinkling the collar portion, typically after attachment of the film cap to the applicator. The top portion of the film cap is also substantially free of wrinkles, except for optionally tension wrinkles, although these may also be removed.

The film cap may be attached or joined to any part of the applicator, typically the first applicator unit, including the bottom side, interior or exterior thereof, by any securing means. The area of the film cap, which is attached, is herein also referred to as attachment region of the film cap, and this is preferably the collar portion. Preferred may be that the film cap is at least attached to the inside (tampon facing) or outside of the applicator unit containing the tampon. Typically, the film cap is not attached to the tampon.

Exemplary methods are described hereinafter. Preferred securing means include heat seals, and adhesives. For the purpose of the invention, the cap can be secured in just one point, several points or across a broad area as long as the cap is securely attached to the applicator. It is beneficial when the securing means is such that it can withstand a force of at least 125%, or even at least 150% or even at least 175% of the average maximum expulsion force of the arrangement, as set out above.

This can be determined by any known method for force determinations, for example by a modified version of the method and measuring device set out above to determine the maximum expulsion force and the tampon exposure moment of rupture. This test is done such that the portion of the film cap, which is not attached to the applicator, is re-enforced, so that it will not rupture when the maximum expulsion force is reached, nor when a multiple of this force (e.g. twice this force) is reached, to avoid that rupture takes place prior to release of the film cap from the applicator unit in its attachment point. For example, typically the collar portion of the film cap is attached to the applicator and the top portion is not, and only the latter is reinforced, such as reinforcing with pressure sensitive tape comprising a high tensile strength backing substrate.

First the average maximum expulsion force is determined for the (unmodified, non-reinforced) arrangement. Then, the reinforced arrangement is pushed with a constant speed and it is measured what the force is at the moment that a piece of the film cap becomes detached from the applicator unit, which can be observed by camera and recorded video, whereafter the above % of the maximum expulsion force that the cap attachment can withstand, can be calculated by using the previously measured average maximum expulsion force. Alternatively, the experiment can be done until the moment a specific force is reached, e.g. 150% of the maximum expulsion force, and it can then be observed if the film cap has become detached from the applicator (or not).

Figure 1B:
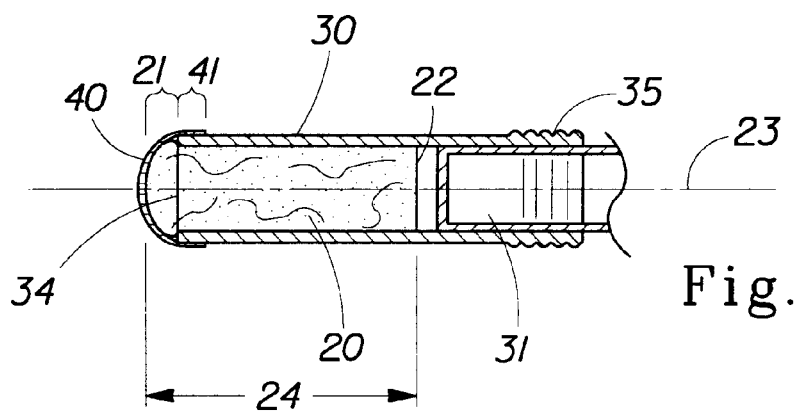
FIG. 1b is a cross-sectional view of a part of another preferred arrangement of the invention.

The above described cap security check is to confirm that the cap will not detach inside the body when expelling the tampon from the applicator. If the cap is similar in design as shown in FIGS. 1a and 1b, cap security as described above is a test of the attachment's shear strength.

Depending on the situation, to avoid unintended separation of the cap outside the body (e.g. before use), the attachment can use materials and points of attachment to minimize possible peel-off, starting from the base of the collar, up to the top portion of the film cap. A preferred design is where the cap collar, at least near its base or bottom edge, is attached to the applicator substantially about its periphery.

Process for Making the Arrangement

The process for making the film cap involves shaping a planar film into a film cap. The planar film, as used herein, is a film which can be placed in or conform to a single plane, without deformation, other than light pressure or tension or gravitational force, for example as required to straighten a film when unrolled from a roll. The film may also be a planar film laminate, formed from a number of layers of substrate material. The film may also be a planar film made from a number of sheets joined together at the edges with lap or butt joints. However preferably the film is a single sheet or laminate sheet measured in the required size.

The film preferably does not comprise any seams, welds, or not even wrinkles, just prior to the first step of the process to make the film cap. The process herein is such that this planar film, or part thereof, can be used immediately to form the film cap. Thus, the planar film is typically directly placed in close contact with a mould. Any type of tool, which has at least one moulding surface that acts to shape a film into a self-sustaining shaped film cap, pre-film cap or part thereof, can be used.

Preferred moulds are moulds which have the shape and dimensions of, or suitable to form, the tampon or applicator unit. Preferred are male or female moulds, such as male or female moulds of the tampon, or the applicator unit, or part thereof. The moulds may be optionally heated or cooled as needed. Preferred may also be that the tampon or applicator unit itself is used as mould. Female moulds used in concert with a male mould as a 'plug assist' illustrates another mould technique that may be utilized. The male mould may comprise a separate tool or part of the applicator and/or tampon itself.

Further moulds that combine male and female elements may be employed, in particular as an additional means to control the shape formation and/or location and degree of thinned areas. An example is a vacuum male mould, cylindrical in shape with a concave female mould element at the top. The result is a top portion, which is inverted inside the collar portion and which is later inverted or pushed outwards to form a convex top portion, when it is placed over a dome-shapes tampon or applicator unit. This top portion is then thinned.

The process of shaping the film over or in a mould may be done by any conventional method (including thermoforming, cold-forming and other plastic yield deformation techniques), and typically depending on the film type used, a specific method may be most preferred. Cap shaping may occur in a single manufacturing operation. An example of this is creating a film cap, which is then positioned in or over the tampon of applicator unit and optionally further shaped, by for example stretching the film cap further, or strain hardening the film cap.

Preferred may be that the process involves plasticizing of the film and/or more preferably heating of the film, to at least shape the film, prior, simultaneous or subsequent to positioning the film in close contact with the mould. For example, the film may be deformable when plasticized with a specific liquid, and then, this step facilitates the shaping of the film. Preferred may be that the liquid is a plasticizer or solvent for the film, or part thereof, for example that the film is soluble in water or glycerol and that the liquid comprises respectively water or glycerol, or that the film is plasticized by water or glycerol and the liquid is water or glycerol. An example of a film that can be plasticized by water is a cellophane that includes also hydrophilic agents such as glycerol.

More preferred is that the film is deformable when heat is applied and the process involves application of heat. Any source of heat can be used, including placing the film in close contact with a heating element, placing the film along or through hot air, using a heated mould, etc.

Equally preferred may also be that the process involves the application of a force onto the film, to shape the film, typically by plastic yield strain, optionally combined with heating, dissolving, plasticizing or wetting of the film. Preferred may be that air pressure or a vacuum is applied onto the film.

Thereto, the male and/or female or otherwise shaped mould may be provided with a pressure or vacuum source, to facilitate the formation of the film cap. The mould may be air permeable, or may comprise small openings such as (pin) holes, slits etc. For example, the vacuum may be unevenly applied on the film, so that the film is more stretched where more vacuum is applied. Those selected areas that have been more stretched (or strained) form weakness areas, and these further control the expulsion (force) of the tampon through the film cap.

Generally, those areas of the film cap that have been stretched or strained via plastic yielding also display a reduced thickness of calliper. Therefore, one way to determine if an area has been stretched (compared to the original film) or stretched more in one area compared to another, is to measure the calliper film gauge as described herein.

The holes or slits in a mould may be positioned in a selected place or pattern, to provide the desired pattern of weakness areas. For example, the part of the mould which forms the top portion of the film cap may comprise one or more vacuum holes or slits, so that areas of the top portion of the film cap are more stretched then the collar portion of the film cap, resulting in an area or pattern of weakness in the top portion of the film cap. The process can also be operated such that the area of weakness is not just a thinned area but actually a breach in the film cap, such as a hole, perforation or slit.

The process also comprises the step of attaching the film cap to the applicator, typically to the (first) applicator unit. This attachment step may be done by any method, suitable to attach the film cap to the applicator in such a manner that the film cap is not released when the expulsion forces as set out herein are applied to the film cap. The preferred method will typically depend on the type of material used for the film cap and/or for the applicator.

Preferred methods include mechanical attachment such as by example puncturing or embedding parts of the film cap into the applicator, using mechanical fastening means including the hoop tension of the film cap itself, elastic or adhesive tabs or bands. Also preferred process steps to attach the film cap to the applicator involve wetting, or more preferably heating the film in at least the area to be attached to the applicator, and/or heating the applicator, in at least the area to be attached to the film cap. Suitable methods involve the heating and wetting methods described above.

The film cap or film may also be attached by use of an adhesive or cohesive, applied to at least part of the area of the film cap which is to be attached, and/or to at least part of the area of the applicator which is to be attached.

The film cap or film may also be attached by application of a material to invoke epoxy bonding, use of pressure, or even allowing a coating on the applicator, for example wax, to be absorbed by or intermingled with pores of the film cap, if present.

The film or film cap may be attached prior to, simultaneous with or after film cap shaping. The film or film cap may be attached to any internal or external part of the applicator.

In the case when the film cap is formed before attachment to the applicator, often the film cap needs to be first positioned, before attachment, over or into a portion of the applicator as well as over or next to a portion of the tampon if present, generally the tampon head. Positioning of the film cap may include movements such as bringing the cap next to a portion of the applicator and/or tampon, sliding or pulling the cap over a portion of the applicator and/or tampon, or rolling the cap onto or over a portion of the applicator and/or tampon.

Rolling can include the inversion of the film cap over a portion of the applicator and/or tampon. For example, when the tampon is already present in the applicator, the part of the film cap that is to correspond to or contact the top of the tampon in the final article is initially brought in contact with the top of the tampon, thereafter the cap is inverted (i.e. turned inside out) while rolling successive regions of the cap down the tampon and applicator surfaces. If desired, the cap can be pre-inverted prior to the above-described inversion process such that when the above-described inversion process is completed, the film cap is essentially partially or fully re-inverted or un-inverted back into the general shape orientation as existed when the cap was formed on or in the mould.

Any excess film, not needed as part of the final film cap, may be removed, prior, simultaneous or subsequent to the shaping step, or more preferably, the attachment step. This may be done by any known method, including cutting excess film with a blade, probe, or knife or a laser, or by use of an air-knifing or water-knifing step or heated knife or probe.

Thus, in one preferred embodiment herein, the process is done by shaping the film over a male mould, the male mould including the tampon and/or applicator and/or applicator unit itself, or a mould having a similar shape to the tampon, applicator unit and/or applicator.

For precision of the process and/or control of the product quality, it may be preferred to shape the film directly over the tampon or applicator/unit. Also, this may simplify the process, because the film cap is then directly in the required position, to be attached to the applicator. However, for practical process reasons it may be preferred to use a separate mould for the shaping step. As an example to further illustrate the flexibility of the process, the film (or a partially-formed film cap) can be first attached to one end of the applicator (e.g. a tube) to create an interim cap, such as a flat top cap when starting with film. Then a male mould (either a separate tool or the tampon itself) can contact and press into the film located across the applicator opening to cause the film to be shaped (e.g. by plastic yielding) into the cap shape. The male mould can contact and engage the film from either the top or bottom surface of the film. If engaging the bottom surface, the mould can be introduced through the applicator to contact the film.

The male and/or female or otherwise shaped mould may be provided with a vacuum source, to facilitate the formation of the film cap. Hereto, the mould may be air permeable, or may comprise small openings such as (pin) holes, slits etc. The vacuum may be unevenly applied on the film, so that the film is more stretched where more vacuum is applied. Then selected areas form weakness areas, having a reduced thickness, which further controls the expulsion (force) of the tampon through the film cap. Such areas may even be sufficiently thinned to actually comprise breaches in the film cap such as holes or slits.

Thus, the holes or slits in the mould may be positioned in a selected place or pattern, to provide the required pattern of weakness areas. For example, the part of the mould which forms the top portion of the film cap may comprise more vacuum holes or slits, so that the top portion of the film cap is more stretched or plastically yielded (thinned) than the collar portion of the film cap, resulting in an area of weakness in the top portion of the film cap.

A mould may be made of any material and be externally textured or smooth, solid, or internally chambered, or porous in nature. Preferred moulds are air permeable and/or (micro-) porous. Preferred may for example be a micro porous, air permeable mould, made of aluminium and epoxy aggregate, such as for example Metapor BF100Al, available from Portec Ltd, Switzerland. Highly preferred moulds comprise heat resistant, non-sticky, non-oxidising material. Non-oxidising materials include stainless steels and polymers.

The size and shape of the male mould will depend on the size and shape of the film cap which is produced, which will again depend on the size and shape of the tampon, applicator and/or applicator unit, as well as any later process steps, such as a post stretching process step. When the film cap is to be attached to the exterior of a cylindrical applicator unit, a male mould has for example typically the same or slightly larger diameter than the exterior diameter of the applicator unit. However, the film cap may be stretchable, in which case a film cap with a smaller diameter can still be suitably attached to the exterior of the applicator unit.

If the film cap is to be attached to the interior of a cylindrical applicator unit, then a male mould may have a diameter which is just larger than the diameter of the tampon, and/or just smaller than the interior diameter of the applicator unit.

For certain plastic yieldable films, a male mould may be used without vacuum employing mechanical stretching. For a female moulding process, it may be preferred that a combination of mechanical stretching and vacuum (or alternatively air pressure) is used, and this may aid creation of weakness areas. It may also aid to anchor the film at different points during the process to cause controlled straining of the film at different points as a mechanical stretch force is applied.

Preferred areas of weakness created in the processes herein is a cross-pattern on the top portion of the film cap, which does not have any breaches. The areas of weakness can also be made by mechanical puncture, needle punching, mechanical slitting, mechanical embossing, cutting, hydroforming, flame perforating, spark discharge aperturing, vacuum forming, water knifing, hot air perforation, laser perforation/cutting, or ultrasonic energy tools.

The areas of weakness may have a pattern, such as a pattern of thin lines or spots. They may be in any shape, including straight or curved or zigzag. The areas of weakness may be present in the film, prior to shaping the film cap, including thinned areas, holes, perforations or slits.

As mentioned above, the cap shaping process can involve more than one process step, including for example a post stretching step, when a film cap is made with a mould and placed on or over a tampon or applicator unit and whereby then the film cap is further stretched (and thinned), e.g. prior to, during or after attachment of the film cap.

The process may also comprise the additional, optional step of making the film cap, or part thereof, typically the collar portion, smoother. This can be done by any method, for example by post stretching as described above, heating part or all of the film cap and/or applying pressure on part or all of the film cap, or further coating part or all of the film cap, for example with wax. Then, undesirable wrinkles, even if under tension, can be smoothened out or over.

Examples of Processes

EXAMPLE 1

Male Molding Process

An open ended flushable applicator is provided, which has two telescoping applicator units, a first unit being the inserter tube holding the tampon and the second unit being a pusher tube, having a smaller exterior diameter than the interior diameter of the inserter tube. The pusher tube enters the inserter tube at the opposite end to the expulsion open end of the inserter tube, through which the tampon will be expelled. The pusher tube serves to push on the back end of the tampon to expel the tampon through the open expulsion end of the inserter tube. The tubes are produced from a spiral-wound paperboard construction, coated on the exterior with a wax-based coating. For example, the inserter tube may be 66 mm long and have an internal diameter of 15 mm. The pusher tube may have a length of 73 mm. The tampon may be 50 mm long and compressible, so it fits with in the inserter tube.

The open end of the inserter tube is then covered by a film cap. The film cap is shaped and attached as follows. A male mandrel, in the form of the cylindrical tampon with rounded top portion or side, is machined from Metapor BF 100 AL material (a micro-porous, air permeable aluminum and epoxy aggregate material by Portec LTD Switzerland), to a diameter just less than the interior diameter of the inserter tube. Due to the material's inherent porosity, the mandrel can be coupled with a vacuum source as desired. In a preferred execution, the vacuum is only applied at the surface of the upper (e.g. forming the top portion of the film cap) ⅓part of mandrel, the surface of the lower ⅔rds of the mandrel may for example be coated (painted), to seal the surface pores. The bottom of the mandrel is left open to later contact a vacuum platen in order to transfer vacuum to the top of the mandrel. At the top of the mandrel are four slots cut and when the vacuum is applied, the film is drawn into these the slots during cap formation.

A block, which has in its center a vertical hole that has a slightly larger diameter and shorter length than the outer diameter and the length of the inserter tube, is also machined from the afore-mentioned Metapor material. With the exception of the surface of the bottom and the surface of the centered hole of the block, the surface pores of the block are taped over to prevent any air or vacuum transfer.

The first applicator unit or inserter tube, not comprising a tampon, is placed over the mandrel, such that the bottom of the mandrel and the inserter tube are even. The mandrel, inserter tube, and block are positioned within a fixture, which rests on a vacuum platen by which vacuum is pulled via the bottom, through the interior walls of the hole of block, as well as through the portion of the top of mandrel and its four slots, extending through the open end of the inserter tube, and thus not covered by the inserter tube.

Above the fixture is a film-holding fixture, which can hold the film under tension and which can be positioned over the mandrel-block assembly, to hold the film in a generally horizontal plane which is generally orthogonal to the vertical orientation of the mandrel-inserter combination within the block.

The film is placed in this fixture. For example, the film may be cast film of a LDPE/LLDPE/$TiO_2$ blend, available as DH215-Sofflex from Clopay Corporation (Cincinnati, Ohio, USA), being embossed and having a gauge thickness of 38 microns and a tensile strength of 20N/25.4 mm.

In preparation for forming the film cap, the vacuum platen is lowered such that when the film fixture is swung down into the horizontal position, covering the mandrel and block, the top of the mandrel does not contact the bottom surface of the film. A radiant thermal heater is positioned above the surface of the film in the film fixture, which does not face the mandrel. The film is thus heated to its softening point at which time the thermal heater is moved away from the film. Then, the vacuum platen is raised as to push the forming fixture with the block and mandrel and inserter tube into the film (from below; on the opposite side to heater). The film then shapes around the top surfaces of the forming fixture, including the part of the mandrel, which extends through the opening of the inserter tube, and at least part of the inserter tube. Preferably, this is done with assistance from the vacuum being pulled through the forming fixture and in particular the slots (where the film is pulled somewhat into those slots). The formed film cap, around the exposed part of the mandrel and the top 18 mm of the inserter tube is then allowed to cool.

The combined inserter tube, mandrel are then removed from the block with the formed film still attached. Because of the stretch process profile occurring especially in the collar portion, the hoop tension about the top 18 mm of the inserter tube may be sufficient to hold the film cap securely attached in place.

In addition to the hoop tension to keep the film cap in place, additional attachment means may be used, such as the use of adhesives. For example, before contacting the film to the mandrel-tube combination, a spiral pattern of adhesive may be applied to the tube or the film, e.g. Bostik Findley H2031 pressure sensitive adhesive may be placed on the top 7.5 mm of the tube at an average basis weight of 0.00093 grams $cm^2$. After the collar is shaped from the film around the upper part of the inserter tube, the film cap can be pressured into the adhesive to get a more secure attachment.

The formed film comprises the film cap and excess film, which is removed, for example by cutting with a knife to leave a trimmed collar. In this example, the collar portion is preferably no longer than 18 mm long, so that the entire collar is held onto the tube by at least hoop tension. The collar may preferably be cut to 7.5 mm, so all is held by hoop tension and adhesive.

Additional lines of weakness can be made in the cap, such as four slits by use of a knife blade before removing the cap from the mould. The tampon is then placed into the inserter tube, followed by positioning of the pusher tube.

The film cap-forming step may also be a so-called cold-stretch forming step in contrast to vacuum thermoforming, described above. The same steps as described above may then be used, except the vacuum and the heating steps. Then, the resulting film cap has negligible thinning or plastic yielding at the top, and progressively increasing yielding or stretch (and film thinning) in the direction of the collar portion, but again less yielding or stretch (and less thinning) at the bottom of the film cap.

This can be observed by drawing a grid on the film, prior to the film cap formation and observing the patterns of the grid after film cap formation.

EXAMPLE 2
Female Molding Process

An open ended flushable applicator is provided, which has two telescoping applicator units, a first unit being the inserter tube holding the tampon and the second unit being a pusher tube, having a smaller exterior diameter than the interior diameter of the inserter tube. The pusher tube enters the inserter tube at the opposite end to the expulsion open end of the inserter tube, through which the tampon will be expelled. The pusher tube serves to push on the back end of the tampon to expel the tampon through the open expulsion end of the inserter tube. The tubes are produced from a spiral-wound paperboard construction, coated on the exterior with a wax-based coating.

For example, the inserter tube may be 66 mm long and have an internal diameter of 15 mm. The pusher tube may have a length of 73 mm. The tampon may be 50 mm long and compressible, so it fits with in the inserter tube. The open end of the inserter tube is then covered by a film cap. The film cap is shaped and attached as follows.

A female mould comprising a multitude of cavities in the form of the cylindrical, rounded tampon, or inserter tube, is machined from Metapor BF 100 AL material (a micro-porous, air permeable aluminum and epoxy aggregate material by Portec LTD Switzerland), to a diameter just greater than the external diameter of the inserter tube. The cavities have typically rounded edges at the surface of the mould. For example, the cavities may be 1.65 cm deep; have a curving cylindrical side wall, e.g. with a curvature of 0.64 cm radius at the bottom of the cylindrical side wall to transition to the bottom surface with a 0.34 cm diameter, whilst at the top a curvature of a 0.51 cm radius transitions the side wall to the top surface of the mould.

The female mould is connected to a vacuum thermo former, such as available from Formech Company, UK. Due to the material's inherent porosity, the mould can be coupled with a vacuum source as desired, or extra holes or slits may be made in the mould, to draw the vacuum through. For example, the cavities may have cross-pattern(s) at the bottom, through which the vacuum can be applied. The vacuum pulling and heating can be done as described above.

The film (e.g. 25×25 cm) is held in a film holder in tension and placed above the openings of the cavities of the mould, under the heat source. The radiant heat source is switched on, to soften the film, for example for 3 seconds. Then, the vacuum source is switched on, pulling the softened film into the cavities. However, this may also be done simultaneously, or the film may be partially pulled into the cavities first by the vacuum, and then heated, to pull the film even further into the cavities. The film is allowed to cool and then the vacuum is switched off. The cooling may be assisted, for example by passing of cold air over the film and mould.

The shaped film caps can then be removed from the female mould and cut loose from one another. They are then attached to the applicators, e.g. to the inserter tube's inside or outside cylindrical wall, preferably by use of adhesives on the wall portion to be attached to the collar portion of the film cap, as described above.

Excess film may be cut away. Also, additional areas of weakness (in addition to the thinned areas formed in the top of the film cap, due to the vacuum applied thereof, e.g. the vacuum through the cross-pattern) may be formed, for example by cutting perforation lines or score lines into the (topside) of the film cap.

Of course this process may be modified in many ways, including heating of the mould (rather than the film or in addition to the film), cooling of the mould (passing of cold fluids through the mould), combination use with a male mould (plug assist), different films, sizes, cavity-curvatures, etc.

The following is a description of preferred tampon-applicator arrangements of the invention, referring to the figures. FIG. 1a shows a tampon-applicator arrangement 10 in perspective view. The applicator has a first applicator unit 30 with a finger grip 38, and containing also a plunger or pusher part 32 and typically made by plastic moulding. Inside the first applicator unit 30 is a tampon 20, which partially extends from the applicator unit, i.e. with its tampon top portion 21. This is made visible in FIG. 1a through the cut out section. The tampon 20 has a slightly smaller diameter than the interior diameter of the first applicator unit 30. The tampon 20 is cylindrical, with a round or dome-shaped top portion 21; the bottom side may be any shape, but is typically about flat.

While holding the finger grip 38, the arrangement 10 can enter the body by pushing the leading portion of unit 30 past the labia and into the vagina. While continuing to hold the grip 38, the plunger 32 can be pushed inwards, to push the tampon 20 out of the first applicator unit 30. The applicator may be made of any material, for example of cardboard or plastic. The tampon 20 may comprise a cord or string (not shown), which serves to pull the tampon out of the vagina after use. This string is typically attached to the interior of the tampon 20 and extends from the tampon's bottom side, typically through the finger grip 38 and optionally through the plunger 32.

The top portion of the tampon 21 is covered by a film cap 40, which is in contact with the entire tampon top portion 21. The film cap 40 extends further than just the top portion of the tampon 21, namely with a portion, the herein referred to collar portion 41, which is attached to the outside of the first applicator unit 30, such that the collar portion 41 includes or forms an attachment zone on said applicator unit 30. The film cap 40 is moulded such that its shape and dimensions conform to the tampon top portion, whereby of course its dimensions are about the same as the top portion of the tampon 21, such that the film cap 40 fits very snug over the tampon top portion 21. This may be done by any of the moulding processes described above. In FIG. 1a it is shown that the film cap 40 is in contact not only with the entire tampon top portion 21 but that the entire collar portion 41 of the film cap 40 is in contact with part of the first applicator unit 30. Thus, a uniformly applied film cap 40 is provided, which no uneven areas. Moreover, the film cap 40 is formed from a single planar film material, moulded in the shape of the tampon and therefore, it has no seams or welds which otherwise could create sharp edges.

The collar portion 41 of the film cap 40 may be slightly further stretched when attaching it to the first applicator unit 30. The collar portion 41 may also be strain hardened prior to attachment or after attachment; and/or it may be de-wrinkled, as described herein above.

The attachment may preferably be done by heat sealing or by use of adhesive, which is applied on the collar portion or preferably on the part of the first applicator unit 30, which is to be connected to the collar portion 41, as described above.

The film cap 40 has, as areas of weakness, 5 lines of perforations 50, dividing part of the film cap 40 into 5 identical film petals. Typically, the lines of perforations 50 are located on about the part of the film cap which is in contact with the tampon top portion 21, up to the edge of the collar portion, although they may not extend that far, or they may extend onto the collar portion 41.

In FIG. 1a, the lines of perforation 50 converge at the top of the film cap 40 (and of the top of the tampon 21), but it may be preferred that the top of the film cap does not contain any perforation 50.

Of course, the film cap 40 may equally comprise a different number of lines of perforations 50, for example 6, 4 or 3. The film cap 40 may also comprise different types of areas of weakness, such as patterns (lines) of thinness, score lines etc. The film cap 40 may also comprise areas of weakness, which divide the film cap in non-identical petals. In one embodiment the film cap comprises one or more areas of weakness, which is or are areas where the film is thinned in a non-specific pattern, due to the forming process, e.g. due to stretching of the film when forming the film cap 40, for example by the application of vacuum or heat on the film and then pulling, and thereby stretching, the film in a female mould, in the shape of the tampon 20 (top portion 21).

It is important for the best execution and wear experience, that the areas of weakness are such that when the film cap 40 ruptures when the tampon 20 is expelled through the film cap 40, out of the first applicator unit 30, that no parts of the film cap come loose from the applicator unit.

FIG. 1b shows a schematic cross-sectional view of the top part of another arrangement of the invention comprising wound cardboard tube units, similar to the arrangement 10 of FIG. 1a, except that the applicator has also a second applicator unit 31, but no plunger, whereby the second unit 31 can be pushed inside the first unit 30, to push the tampon 20 out of the first unit, in a manner as described above. In FIG. 1b, only the first applicator unit 30 is fully shown, with the leading portion of the second unit 31 depicted inside a portion of the first unit 30 in the end where the grip 35 is located. The film cap 40 is formed and attached as in FIG. 1a, described above.

The tampon 20 has a tampon top portion 21, which extends from the leading edge or top edge 34 of the first applicator unit 30. The tampon 20 and applicator unit 30 have each a longitudinal axis, along line 23 and the tampon has a length 24, which equals the distance from the point where the longitudinal axis 23 crosses the top of the tampon 20 to the point where the axis 23 crosses the bottom side of the tampon 22.

The part of the tampon exposed in FIG. 1b is the part of the tampon from the leading edge 34 to the point where the longitudinal axis 23 crosses the top of the tampon, which equals here the tampon top portion 21.

Figure 1C:
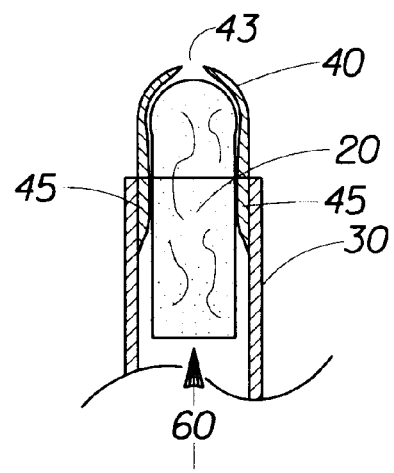
FIG. 1c is a cross-sectional view of a part of an arrangement as in FIG. 1b in use.

In FIG. 1c, a part of the arrangement of the invention is shown, whereby the film cap 40 is attached with attachment areas 45 to the interior of the applicator unit 30, which is only partially shown. The film cap 40 conforms to the tampon 20, up to the point it is attached to the applicator unit 30. As shown in FIG. 1c, when the tampon 20 is pushed out of the first applicator unit 30 with a force applied from the bottom, along force line 60, the film cap 40 may extend before it forms the first indication of a rupture area 43. The average maximum film extension is thus measured by the method described, measured up to the point 43.

Figure 2A:
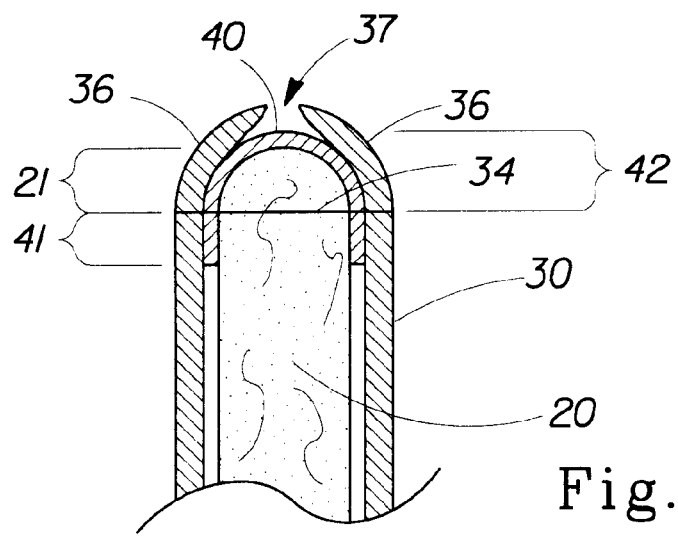
FIG. 2a and is a cross-sectional view of part of other preferred embodiments of the invention.

Once the film cap 40 ruptures, the tampon 20 leaves the first applicator unit 30 generally under a reduced pushing force. FIG. 2*a* shows a cross sectional view of part of an arrangement of the invention with an alternative film cap 40 construction and an alternative first applicator unit 30 construction, which is only partially shown. The first applicator unit 30 has a number of applicator petals 36, which extend from the line 34 of the unit 30, this line 34 being the horizontal line through the bottom edges of the petals 36. The petals 36 converge almost above the top of the tampon 20, leaving a small gap 37 at the top. When the tampon 20 is pushed upwards, for example by a second applicator unit or plunger (not shown), as described above, the petals 36 open, to let the tampon through, into the vagina.

The film cap 40 is formed over the tampon 20, or inside the applicator unit 30 and thus lays between the tampon 20 and the applicator unit 30. At least the top portion 42 of the film cap 40 is in contact with the entire tampon top portion 21 (part of the tampon 20 extending beyond the line 34 of the first unit 30), and is thus uniformly applied. The film cap is formed by a method described above for FIG. 1 and there are no uneven areas, nor any welds or seams.

Figure 2B:
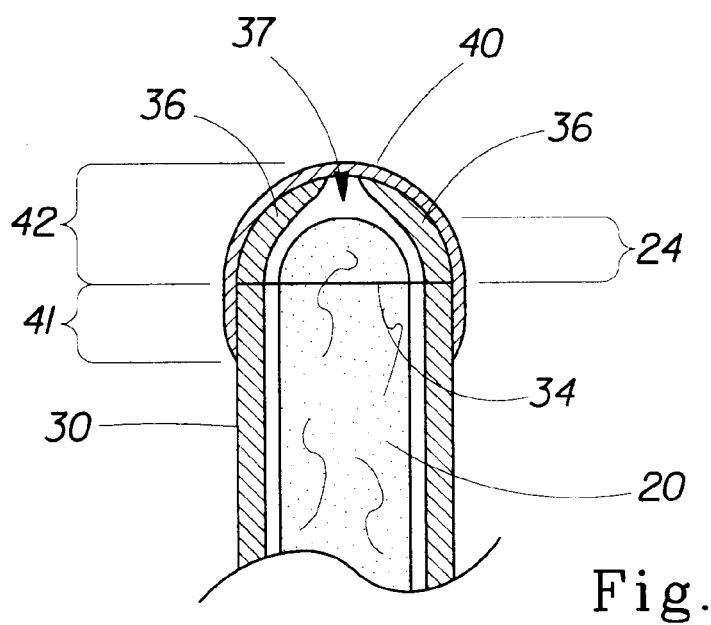
FIG. 2b is a cross-sectional view of part of other preferred embodiments of the invention.

The collar portion 41 of the film cap is attached to the inner wall of the first applicator unit, by any method described herein, e.g. pressure sensitive adhesive. FIG. 2*b* shows a cross sectional view of part of an arrangement of the invention with an alternative film cap 40 construction, compared to FIG. 2*a*. The applicator unit 30 has again a number of applicator petals 36, extending from the line 34 of the unit 30, just as in FIG. 2*a*. However, the film cap 40 is positioned over the unit 30 and the petals 36 thereof.

In the area where the film cap 40 is present, the film cap 40 is in contact with the entire applicator unit 30, except of course where there is a gap 37 in the top of the applicator unit 30 (of course, in the area of the gap 37 there is no part of the applicator unit 30 itself, so the film cap 40 can not be in contact with the unit 30). Thus, for the purpose of the invention, the film cap 40 is uniformly applied onto the applicator unit 30. The film cap 40 thus conforms to the shape and dimensions of the applicator unit 30, as described above. The film cap is formed by a method described above for FIG. 1; there are no uneven areas, nor any welds or seams.

Figure 3A:
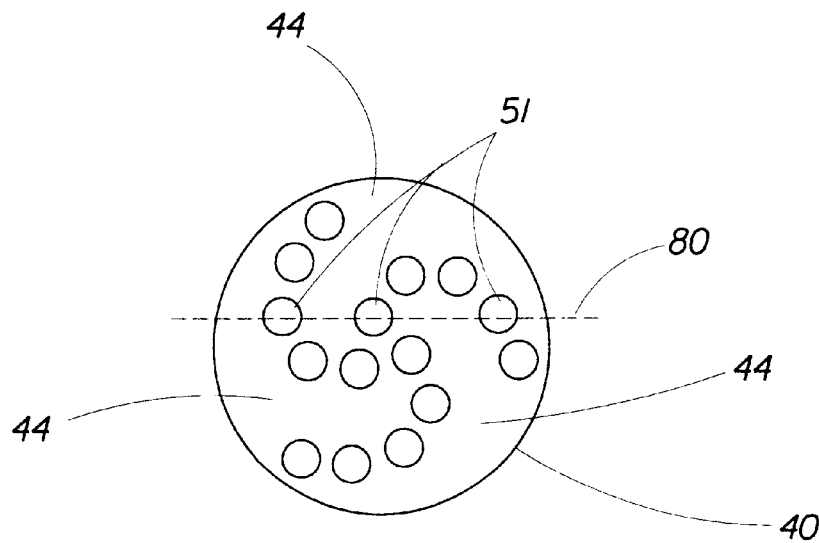
FIG. 3a is a top view of a preferred arrangement of the invention.

The collar portion 41 of the film cap is attached to the outer wall of the first applicator unit 30, by any method described herein. FIG. 3*a* shows a top view of an alternative film cap 40, having lines of weakness in the form of lines of thinned areas 51, in this preferred embodiment in a spiral configuration. The lines of thinned areas define film cap petals 44, which will detach from one another, to thus provide the film cap 40 to rupture. The thinness areas 51 can be made by any method, for example by embossing a film with the pattern prior or after the film cap 40 is formed, for example by application of pressure and heat with a tool with the specific pattern. The tooling can also be integrated with the cap shaping mould.

Figure 3B:
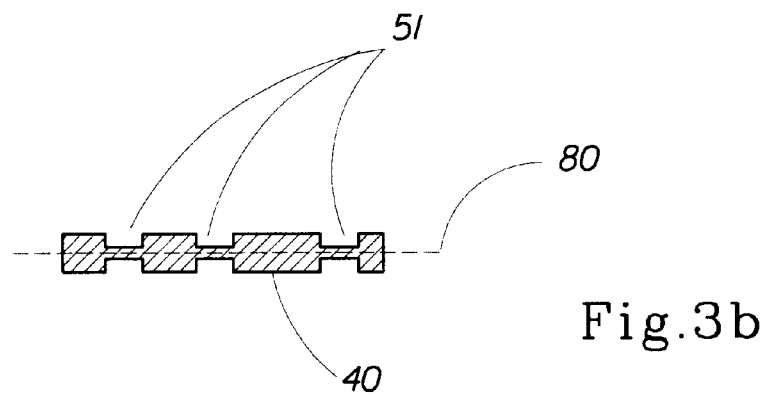
Figure 3C:
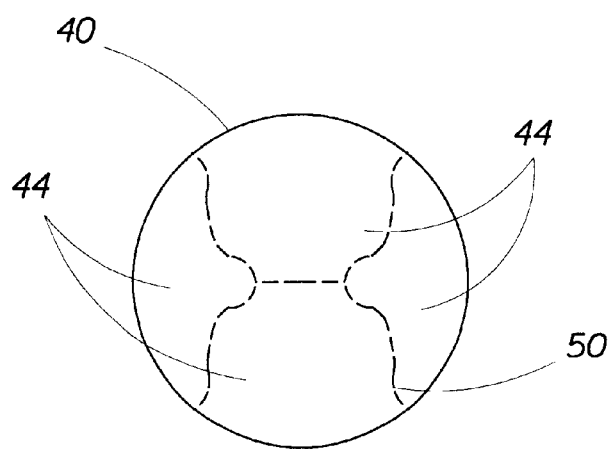
FIG. 3c is a top view of another arrangement of the invention.

FIG. 3*b* shows a cross sectional view of the film cap 40, along the cross section line 80 in FIG. 3*a* showing the thickness variations therein, and showing the 3 thinness areas 51 which lie on the cross section line 80. FIG. 3*c* shows another top view of an alternative film cap 40, having lines of weakness in the form of perforations 50, defining film cap petals 44 of different width and length. The petals 44 will detach from one another, to thus provide the film cap 40 to rupture. The perforations 50 can be made by any method, for example by cutting the film with the pattern prior, during or more preferably after the film cap 40 is formed, for example by use of a specific cutting tool (knife blade) or by application of heat with a tool with the specific pattern.

Figure 4:
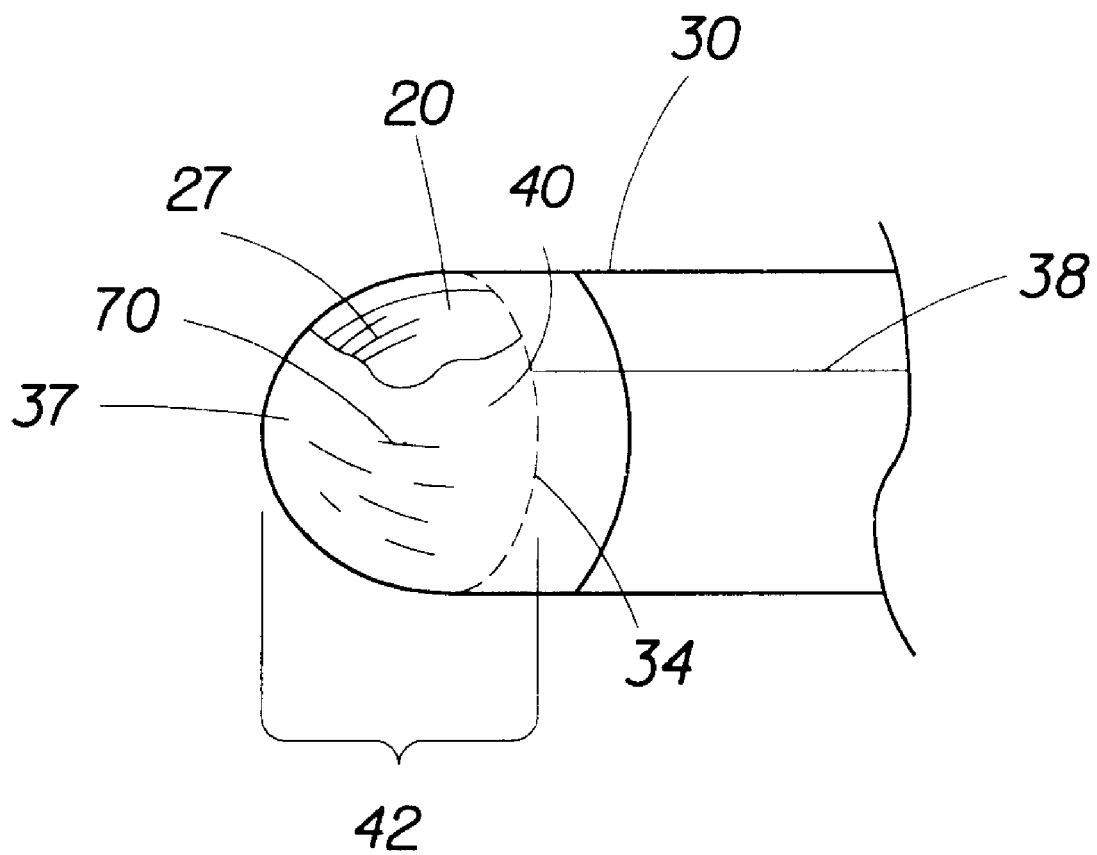
FIG. 4 shows a perspective view of the top portion and part of the collar portion of a preferred film cap and the tampon and applicator unit covered thereby.

FIG. 4 shows a perspective view of a part of the arrangement of the invention. The open-ended applicator unit 30 has a gap line 37, running longitudinally along the side of the unit 30, which is covered by the film cap 40, which is attached thereto (a part of the collar portion of the film cap 40 is shown). The film cap 40, positioned over the gap 37 in the applicator unit 30 is uniformly shaped, because it is such that it has the smallest possible surface area over the applicator unit 30, namely it is stretched under tension over the applicator unit 30 and does not follow the gap 37 in the unit.

The tampon top portion (not shown in FIG. 4, but extending from the top of the tampon 20 to the leading edge 34 of the applicator unit 30) is also covered by the uniformly shaped film cap 40, or in fact the top portion 42 thereof. The tampon 20 has also one or more gaps 27, running from the top of the tampon 20 towards the edge 34 of the applicator unit 40. The film cap top portion 42 is uniformly shaped, because the film cap top portion 42 is in contact with the surface of the entire tampon top portion, including (part of) the gap 27. The film cap top portion 42 thus follows the gap area 27 of the tampon top portion.

The top portion 42 of the film cap 40 has a small tension wrinkle 70, due to the formation of the film cap 40, which is done by stretching a film material over a male mould or in a female mould, and due to the fact that the top surface of the tampon has some irregularities and the film cap 40 is attached to the applicator unit 30 under the shaped tension, resulting in tension wrinkle 70. Suitable processes to obtain this are described above. The tension wrinkle 70 may be removed by an addition process step as described herein above, for example by de-wrinkling the film cap, or in particular the collar portion thereof, or by heat shrinking after attachment. However, because the wrinkle 70 hardly extends from the surface of the tampon top portion, and because it is under tension, it does not create any harm during insertion, or problems for the expulsion of the tampon 20 through the film cap 40.

Equally, tampon applicator arrangements of the invention, which have an irregular shaped form, i.e. not a cylindrical collar portion with a smooth, rounded or dome-shaped top portion, can have a film cap with wrinkles under tension, due to the fact that the process of the invention used to make these caps involves stretching the film over these irregular shapes. For example, the top portion of a tampon in an open-ended applicator unit can be concave or mushroom shaped and the film cap is conform to this shape or having the smallest surface area possible to cover this shape, but the forces applied during the shaping step cause one or more small wrinkles under tension, which may be de-wrinkled by a further process step, by any of the methods described herein.

What is claimed is:

1. A tampon and applicator arrangement comprising:

a tampon, an applicator unit, and a film cap, said tampon having a length, a withdrawal end opposed to an insertion end, said insertion end having a top portion;

said applicator unit being capable of receiving a tampon, said applicator unit having a bottom side opposed to a topside;

said film cap being uniformly shaped, said film cap covering at least a portion of said top portion of said tampon and attaching to at least a portion of said applicator unit;

said film cap ruptures upon expulsion of said tampon from said applicator unit during insertion of said tampon; and wherein said tampon and applicator arrangement has an average maximum film cap extension of at least about 20% of said length when the film cap ruptures.

2. A tampon and applicator arrangement according to claim 1, wherein the film cap comprises a formable film.

3. A tampon and applicator arrangement according to claim 1, wherein the film cap comprises a thermoplastic film.

4. A tampon and applicator arrangement according to claim 1, wherein the arrangement has maximum expulsion force to rupture said film cap and expel said tampon through said film cap, said maximum expulsion force ranging from about 700 grams-force to about 2500 grams-force.

5. A tampon and applicator arrangement according to claim 1 wherein said film cap has no folds, welds or seams.

6. A tampon and applicator arrangement as in claim 1 wherein said film cap has areas of variable thickness, the variation in thickness being at least 20% from one area to a second area;

said film cap having a top portion and a collar portion, wherein said top portion is thinner than said collar portion.

7. A tampon and applicator arrangement according to claim 1 wherein the film cap has a collar portion and a dome-shaped, top portion, wherein said top portion is more extensible or stretchable than the collar portion, and said collar portion is strain hardened.

8. A tampon an applicator arrangement according to claim 1, said arrangement being cylindrical, and said film cap having a top portion and a collar portion, said film cap having areas of weakness in the form of one or more continuous or discontinuous lines positioned from the top of the top portion of the film cap toward the collar portion of the film cap.

* * * * *